(12) United States Patent
Haeberle et al.

(10) Patent No.: US 8,999,884 B2
(45) Date of Patent: Apr. 7, 2015

(54) ABSORBENT STRUCTURES WITH COATED WATER-ABSORBING MATERIAL

(75) Inventors: Karl Haeberle, Ludwigshafen (DE); Klaus Dieter Hoerner, Ludwigshafen (DE); Axel Meyer, Schwalbach (DE); Carolyn Ann Spitzmueller, Cincinnati, OH (US); Robin Lynn McKiernan, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/461,039

(22) Filed: May 1, 2012

(65) Prior Publication Data

US 2012/0310196 A1    Dec. 6, 2012

Related U.S. Application Data

(60) Provisional application No. 61/491,930, filed on Jun. 1, 2011.

(51) Int. Cl.
*B01J 20/26* (2006.01)
*A61L 15/60* (2006.01)

(52) U.S. Cl.
CPC ..................... *A61L 15/60* (2013.01)

(58) Field of Classification Search
CPC ................................................ A61L 15/60
USPC .................... 502/402; 264/45.1; 604/372
See application file for complete search history.

(56) References Cited

U.S. PATENT DOCUMENTS

| | | |
|---|---|---|
| 3,479,310 A | 11/1969 | Dieterich et al. |
| 3,905,929 A | 9/1975 | Noll |
| 4,092,286 A | 5/1978 | Noll et al. |
| 4,190,566 A | 2/1980 | Noll et al. |
| 4,541,871 A | 9/1985 | Obayashi et al. |
| 4,666,983 A | 5/1987 | Tsubakimoto et al. |
| 4,959,441 A | 9/1990 | Engelhardt et al. |
| 5,281,683 A | 1/1994 | Yano et al. |
| 5,331,059 A | 7/1994 | Engelhardt et al. |
| 5,409,771 A | 4/1995 | Dahmen et al. |
| 5,532,323 A | 7/1996 | Yano et al. |
| 5,574,121 A | 11/1996 | Irie et al. |
| 5,624,967 A | 4/1997 | Hitomi et al. |
| 5,700,867 A | 12/1997 | Ishiyama et al. |
| 5,837,789 A | 11/1998 | Stockhausen et al. |
| 6,143,821 A | 11/2000 | Houben |

(Continued)

FOREIGN PATENT DOCUMENTS

| | | |
|---|---|---|
| CA | 2078529 | 3/1993 |
| DE | 2730514 | 1/1979 |

(Continued)

OTHER PUBLICATIONS

International Search Report, PCT/US2012/039975, mailed Jul. 16, 2012, 12 pages.

(Continued)

*Primary Examiner* — Colleen Dunn
*Assistant Examiner* — Haytham Soliman
(74) *Attorney, Agent, or Firm* — Andrew A Paul (57) ABSTRACT

Absorbent structures, and absorbent articles with such structures, comprising water-absorbing polymer having a coating of film-forming polyurethane and therein incorporated a hydrophilic silica.

32 Claims, 3 Drawing Sheets

(56) References Cited

U.S. PATENT DOCUMENTS

| | | |
|---|---|---|
| 6,265,488 B1 | 7/2001 | Fujino et al. |
| 6,472,478 B1 | 10/2002 | Funk et al. |
| 6,503,979 B1 | 1/2003 | Funk et al. |
| 6,559,239 B1 | 5/2003 | Riegel et al. |
| 6,657,015 B1 | 12/2003 | Riegel et al. |
| 6,710,141 B1 | 3/2004 | Heide et al. |
| 6,720,389 B2 | 4/2004 | Hatsuda et al. |
| 6,809,158 B2 | 10/2004 | Ikeuchi et al. |
| 6,911,499 B1 | 6/2005 | Brehm et al. |
| 6,979,564 B2 | 12/2005 | Glucksmann et al. |
| 7,183,360 B2 | 2/2007 | Daniel et al. |
| 7,199,211 B2 | 4/2007 | Popp et al. |
| 7,250,481 B2 | 7/2007 | Jaworek et al. |
| 7,993,829 B2 | 8/2011 | Friedman et al. |
| 8,236,715 B2 | 8/2012 | Schmidt et al. |
| 2003/0195293 A1 | 10/2003 | Lubnin et al. |
| 2004/0177513 A1 | 9/2004 | Vreeland et al. |
| 2004/0214937 A1 | 10/2004 | Miller et al. |
| 2005/0033256 A1 | 2/2005 | Schmidt et al. |
| 2005/0043467 A1 | 2/2005 | Bruchmann et al. |
| 2005/0165208 A1 | 7/2005 | Popp et al. |
| 2005/0245684 A1 | 11/2005 | Daniel et al. |
| 2006/0155057 A1 | 7/2006 | Hermeling et al. |
| 2006/0167215 A1 | 7/2006 | Hermeling et al. |
| 2006/0178452 A1 | 8/2006 | Hoefler |
| 2006/0216443 A1* | 9/2006 | Kinoshita et al. .......... 428/32.24 |
| 2007/0043191 A1 | 2/2007 | Hermeling et al. |
| 2008/0027402 A1 | 1/2008 | Schmidt et al. |

FOREIGN PATENT DOCUMENTS

| | | |
|---|---|---|
| DE | 10204937 | 8/2003 |
| EP | 530438 | 3/1993 |
| EP | 955086 | 9/2003 |
| WO | WO 90/15830 | 12/1990 |
| WO | WO 93/21237 | 10/1993 |
| WO | WO 01/45758 | 6/2001 |
| WO | WO 2005/044900 | 5/2005 |
| WO | WO 2006/042704 | 4/2006 |
| WO | WO 2006/082239 | 8/2006 |
| WO | WO 2007/070776 | 6/2007 |
| WO | WO 2009/016055 | 2/2009 |
| WO | WO 2010/054975 | 5/2010 |
| WO | WO 2012/025445 | 3/2012 |

OTHER PUBLICATIONS

International Search Report, PCT/US2012/040062, mailed Sep. 27, 2012, 12 pages.

* cited by examiner

ABSORBENT STRUCTURES WITH COATED WATER-ABSORBING MATERIAL

CROSS REFERENCE TO RELATED APPLICATION

This application claims the benefit of U.S. Provisional Application Ser. No. 61/491,930, filed Jun. 1, 2011, which is herein incorporated by reference in its entirety.

FIELD OF THE INVENTION

The present application relates to absorbent structures, and absorbent articles with such structures, comprising water-absorbing polymer having a coating of specific elastic film-forming polyurethane.

BACKGROUND OF THE INVENTION

An important component of disposable absorbent articles such as diapers is an absorbent core structure comprising water-absorbing polymers, typically hydrogel-forming water-absorbing polymers, also referred to as absorbent gelling material, AGM, or super-absorbent polymers, SAPs. This polymer material ensures that large amounts of bodily fluids, e.g. urine, can be absorbed by the article during its use and locked away, thus providing low rewet and good skin dryness.

Especially useful water-absorbing polymers or SAPs are often made by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of relatively small amounts of di- or polyfunctional monomers such as N,N'-methylenebisacrylamide, trimethylolpropane triacrylate, ethylene glycol di(meth)acrylate, or triallylamine. The di- or polyfunctional monomer materials serve to lightly crosslink the polymer chains thereby rendering them water-insoluble, yet water-absorbing. These lightly crosslinked absorbent polymers contain a multiplicity of carboxylate groups attached to the polymer backbone. It is generally believed that the neutralized carboxylate groups generate an osmotic driving force for the absorption of body fluids by the crosslinked polymer network. In addition, the polymer particles are often treated as to form a surface cross-linked layer on the outer surface in order to improve their properties in particular for application in baby diapers.

Water-absorbing (hydrogel-forming) polymers useful as absorbents in absorbent members and articles such as disposable diapers need to have adequately high absorption capacity, as well as adequately high gel strength. Absorption capacity needs to be sufficiently high to enable the absorbent polymer to absorb significant amounts of the aqueous body fluids encountered during use of the absorbent article. Together with other properties of the gel, gel strength relates to the tendency of the swollen polymer particles to resist deformation under an applied stress. The gel strength needs to be high enough in the absorbent member or article so that the particles do not deform and fill the capillary void spaces to an unacceptable degree causing so-called gel blocking. This gel-blocking inhibits the rate of fluid uptake or the fluid distribution, i.e. once gel-blocking occurs, it can substantially impede the distribution of fluids to relatively dry zones or regions in the absorbent article and leakage from the absorbent article can take place well before the water-absorbing polymer particles are fully saturated or before the fluid can diffuse or wick past the "gel blocking" particles into the rest of the absorbent article. Thus, it is important that the water-absorbing polymers (when incorporated in an absorbent structure or article) maintain a high wet-porosity and have a high resistance against deformation thus yielding high permeability for fluid transport through the swollen gel bed.

Surface crosslinking leads to a higher crosslinking density close to the surface of each water-absorbent particle. This addresses the problem of "gel blocking", which means that, with earlier types of water-absorbents, a liquid insult will cause swelling of the outermost layer of particles of a bulk of water-absorbent particles into a practically continuous gel layer, which effectively blocks transport of further amounts of liquid (such as a second insult) to unused water-absorbent below the gel layer. While this is a desired effect in some applications of water-absorbents (for example sealing under-water cables), it leads to undesirable effects when occurring in personal hygiene products. Increasing the stiffness of individual gel particles by surface crosslinking leads to open channels between the individual gel particles within the gel layer and thus facilitates liquids transport through the gel layer. Although surface crosslinking decreases the CRC or other parameters describing the total absorption capacity of a water-absorbent sample, it may well increase the total amount of liquid that can be absorbed by a hygiene product containing a given amount of water-absorbent during normal use of the product.

There is still a need to provide thinner absorbent articles since they increase the wearing comfort. There has been a trend to remove part or all of the cellulose fibres (pulp) from the products. These ultrathin hygiene articles may comprise construction elements (for example—but not limited to—the diaper core or the acquisition distribution layer) which consist of water-absorbing polymeric particles to an extent which is in the range from 50% to 100% by weight, so that the polymeric particles in use not only perform the storage function for the fluid but also ensure active fluid transportation (in simple words, the capacity of a swollen gel bed to pull liquid against gravity, or wicking absorption, a property that can be quantified as Fixed Height Absorption ("FHA") value, determined as described below) and passive fluid transportation (in simple words, the capacity of a swollen gel bed to allow flow of liquid with gravity, a property that can be quantified as Saline Flow Conductivity ("SFC") value, determined as described below). The greater the proportion of cellulose pulp which is replaced by water-absorbing polymeric particles or synthetic fibers, the greater the number of transportation functions which the water-absorbing polymeric particles have to perform in addition to their storage function. It has been found that for such absorbent articles in particular, there is a need for water-absorbent polymeric particles that have a good absorbent capacity (CRC value) and a good fluid transportation (reflected by a good FHA value and SFC value). Furthermore, it is required that the water-absorbing polymeric particles have a sufficiently high initial uptake rate that can be quantified as Free Swell Rate (FSR). It is well-known in the art that there is a trade-off between the wicking ability and the initial uptake rate.

WO 2009/016055 discloses water-absorbing polymeric particles with high fluid transportation and absorption performance by contacting polymer particles with a post-crosslinker, a nitrogen-containing water-soluble polymer and a hydrophobic polymer and heat-treating the obtained particles.

WO 2006/082239 discloses a water-absorbing material having a coating of elastic film-forming polymers which have high core shell centrifuge retention capacity (CS-CRC), high core shell absorbency under load (CS-AUL) and high core shell saline flow conductivity (CS-SFC).

It is an object of the invention to provide a water-absorbing material having a high active fluid transportation (FHA) and a high initial uptake rate (FSR).

It is a further object of the invention to provide a water-absorbing material having in addition a high core shell saline flow conductivity (CS-SFC).

SUMMARY OF THE INVENTION

The inventors found thereto absorbent structures that contain specific water-absorbing material comprising coated water-absorbing polymer particles obtainable by the steps of:
a) coating water-absorbing polymer particles with an aqueous composition comprising a film-forming polyurethane and hydrophilic pyrogenic silica in a weight ratio from about 5:1 to about 1:5; and
b) heat-treating the coated particles at above 50° C.

Furthermore, the invention relates to absorbent structures that contain water-absorbing material comprising film-coated water-absorbing polymer particles, having a heat treated, e.g. annealed, film coating of a film-forming polyurethane and hydrophilic pyrogenic silica in a weight ratio from about 5:1 to about 1:5.

The water-absorbing material of the absorbent structures herein is such that it swells in water by absorbing the water; it may thereby form a gel. It may also absorb other liquids and swell. Thus, when used herein, water-absorbing' means that the material absorbs water, and typically swells in water, but typically also (in) other liquids or solutions, preferably water based liquids such as 0.9% saline and urine.

DETAILED DESCRIPTION OF THE INVENTION

Hydrophilic Silica

The film-forming polyurethane and the hydrophilic pyrogenic silica may be used in weight ratio from about 3:1 to about 1:4.5, or for example from about 2:1 to about 1:4, in particular 1:1 to 1:4 and preferably 1:1.2 to 1:4.

According to another embodiment, the film-forming polyurethane and the hydrophilic pyrogenic silica are used in weight ratio from about 1:1.3 to about 1:3.

The hydrophilic silica and said polyurethane are applied as a coating prior to the heat treatment step, e.g. that typically serves to evaporate solvents used during coating, and or to form a film, e.g. by so-called annealing, as described below; hence, the coating thus comprises said hydrophilic silica in said polyurethane film.

Hydrophilic pyrogenic silica is well-known in the art, see for example Angew. Chem., 1960, 744-750. It is typically made by "flame hydrolysis" of silicon tetrachloride in a hydrogen/oxygen flame. The particles have a primary particle size of about 10 to about 40 nm, or for example from 10 to 30 nm, and are dispersible in water. Hydrophilic pyrogenic silica is commercially available, for instance under the names of Aerosil or Acematt (by Evonik), or fumed silica (Wacker Chemie).

Useful for the purposes of the present invention are in principle all particulate water-absorbing polymeric particles known to one skilled in the art from superabsorbent literature for example as described in Modern Superabsorbent Polymer Technology, F. L. Buchholz, A. T. Graham, Wiley 1998. The water-absorbing polymeric particles are preferably spherical particles of the kind typically obtained from inverse phase suspension polymerizations; they can also be optionally agglomerated at least to some extent to form larger irregular particles. But most particular preference is given to commercially available irregularly shaped particles of the kind obtainable by current state of the art production processes as is more particularly described hereinbelow by way of example.

The hydrophilic pyrogenic silica may be add as solid to the polyurethane, or polyurethane melt, dispersion or solution.

In some embodiments herein, the pyrogenic silica is added as a solution or dispersion in a liquid to the polyurethane melt, dispersion or solution.

The resulting film coating comprises said silica incorporated in said coating.

In some embodiments herein, further silica, that may also be pyrogenic hydrophilic silica, may be added to the coated water-absorbing polymer particles after the film coating is formed and thus after the heat treatment herein. This is herein considered additional silica material that is not incorporated in the film coating. This additional silica may have any particle size; preferably this is also sub micron. It may be added at an additional weight level of for example 0.01 to 5% by weight of the coated water-absorbent polymer particles.

Water-absorbing material and polymer particles

The coated water-absorbing polymeric particles are preferably polymeric particles obtainable by polymerization of a monomer solution comprising
i) at least one ethylenically unsaturated acid-functional monomer,
ii) at least one crosslinker,
iii) if appropriate one or more ethylenically and/or allylically unsaturated monomers copolymerizable with i) and
iv) if appropriate one or more water-soluble polymers onto which the monomers i), ii) and if appropriate iii) can be at least partially grafted, to give a base polymer,
wherein the base polymer obtained thereby is dried, classified and if appropriate is subsequently treated with
v) at least one post-crosslinker
before being dried and thermally post-crosslinked (ie. surface crosslinked) to give a precursor polymer.

Useful monomers i) include for example ethylenically unsaturated carboxylic acids, such as acrylic acid, methacrylic acid, maleic acid, fumaric acid, and itaconic acid, or derivatives thereof, such as acrylamide, methacrylamide, acrylic esters and methacrylic esters. Acrylic acid and methacrylic acid are particularly preferred monomers. Acrylic acid is most preferable.

The base polymers according to the present invention are typically crosslinked, i.e., the polymerization is carried out in the presence of compounds having two or more polymerizable groups which can be free-radically copolymerized into the polymer network. Useful crosslinkers ii) are disclosed in WO 2006/082239 which is incorporated herein by reference in its entirety.

However, particularly advantageous crosslinkers ii) are di- and triacrylates of altogether 3- to 15-tuply ethoxylated glycerol, of altogether 3- to 15-tuply ethoxylated trimethylolpropane, especially di- and triacrylates of altogether 3-tuply ethoxylated glycerol or of altogether 3-tuply ethoxylated trimethylolpropane, of 3-tuply propoxylated glycerol, of 3-tuply propoxylated trimethylolpropane, and also of altogether 3-tuply mixedly ethoxylated or propoxylated glycerol, of altogether 3-tuply mixedly ethoxylated or propoxylated trimethylolpropane, of altogether 15-tuply ethoxylated glycerol, of altogether 15-tuply ethoxylated trimethylolpropane, of altogether 40-tuply ethoxylated glycerol and also of altogether 40-tuply ethoxylated trimethylolpropane. Where n-tuply ethoxylated means that n mols of ethylene oxide are reacted to one mole of the respective polyol with n being an integer number larger than 0.

Very particularly preferred crosslinkers ii) are diacrylated, dimethacrylated, triacrylated or trimethacrylated multiply ethoxylated and/or propoxylated glycerols as described for example in prior German patent application DE 103 19 462.2. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels in the water-absorbing polymer (typically below 10 ppm) and the aqueous extracts of water-absorbing polymers produced therewith have an almost unchanged surface tension compared with water at the same temperature (typically not less than 0.068 N/m).

Examples of ethylenically unsaturated monomers iii) which are copolymerizable with the monomers i) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers iv) include polyvinyl alcohol, polyvinylpyrrolidone, starch, starch derivatives, polyglycols, polyacrylic acids, polyvinylamine or polyallylamine, partially hydrolysed polyvinylformamide or polyvinylacetamide, preferably polyvinyl alcohol and starch.

Preference is given to base polymers which are lightly crosslinked. The light degree of crosslinking is reflected in a high CRC value and also in the fraction of extractables.

The crosslinker is preferably used (depending on its molecular weight and its exact composition) in such amounts that the base polymers produced have a CRC between 20 and 60 g/g, for example when their particle size is between 150 and 850 microns and the 16 h extractables fraction is not more than 25% by weight. The CRC is preferably between 30 and 45 g/g, more preferably between 33 and 40 g/g.

Particular preference is given to base polymers having a 16 h extractables fraction of not more than 20% by weight, preferably not more than 15% by weight, even more preferably not more than 10% by weight and most preferably not more than 7% by weight and whose CRC values are within the preferred ranges that are described above.

The preparation of a suitable base polymer and also further useful hydrophilic ethylenically unsaturated monomers i) are described in DE-A 199 41 423, EP-A 686 650, WO 01/45758 and WO 03/14300. The reaction is preferably carried out in a kneader as described for example in WO 01/38402, or on a belt reactor as described for example in EP-A-955 086.

It is further possible to use any conventional inverse suspension polymerization process. If appropriate, the fraction of crosslinker can be greatly reduced or completely omitted in such an inverse suspension polymerization process, since self-crosslinking occurs in such processes under certain conditions known to one skilled in the art.

It is further possible to make base polymers using any desired spray polymerization process.

The acid groups of the base polymers obtained are preferably 30-100 mol %, more preferably 65-90 mol % and most preferably 72-85 mol % neutralized, for which the customary neutralizing agents can be used, for example ammonia, or amines, such as ethanolamine, diethanolamine, triethanolamine or dimethylaminoethanolamine, preferably alkali metal hydroxides, alkali metal oxides, alkali metal carbonates or alkali metal bicarbonates and also mixtures thereof, in which case sodium and potassium are particularly preferred as alkali metals, but most preferred is sodium hydroxide, sodium carbonate or sodium bicarbonate and also mixtures thereof. Typically, neutralization is achieved by admixing the neutralizing agent as an aqueous solution or as an aqueous dispersion or else preferably as a molten or as a solid material.

Neutralization can be carried out, after polymerization, at the base polymer stage. But it is also possible to neutralize up to 40 mol %, preferably from 10 to 30 mol % and more preferably from 15 to 25 mol % of the acid groups before polymerization by adding a portion of the neutralizing agent to the monomer solution and to set the desired final degree of neutralization only after polymerization, at the base polymer stage. The monomer solution may be neutralized by admixing the neutralizing agent, either to a predetermined degree of preneutralization with subsequent post-neutralization to the final value after or during the polymerization reaction, or the monomer solution is directly adjusted to the final value by admixing the neutralizing agent before polymerization. The base polymer can be mechanically comminuted, for example by means of a meat grinder, in which case the neutralizing agent can be sprayed, sprinkled or poured on and then carefully mixed in. To this end, the gel mass obtained can be repeatedly minced for homogenization.

The neutralized base polymer is then dried with a belt, fluidized bed, tower dryer or drum dryer until the residual moisture content is preferably below 13% by weight, especially below 8% by weight and most preferably below 4% by weight, the water content being determined according to EDANA's recommended test method No. 430.2-02 "Moisture content" (EDANA=European Disposables and Nonwovens Association). The dried base polymer is thereafter ground and sieved, useful grinding apparatus typically include roll mills, pin mills, hammer mills, jet mills or swing mills.

The water-absorbing polymers to be used can be post-crosslinked in one version of the present invention. Useful post-crosslinkers v) include compounds comprising two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019. Useful post-crosslinkers v) are further said to include by DE-A 40 20 780 cyclic carbonates, by DE-A 198 07 502 2-oxazolidone and its derivatives, such as N-(2-hydroxyethyl)-2-oxazolidone, by DE-A 198 07 992 bis- and poly-2-oxazolidones, by DE-A 198 54 573 2-oxotetrahydro-1,3-oxazine and its derivatives, by DE-A 198 54 574 N-acyl-2-oxazolidones, by DE-A 102 04 937 cyclic ureas, by German patent application 103 34 584.1 bicyclic amide acetals, by EP-A 1 199 327 oxetanes and cyclic ureas and by WO 03/031482 morpholine-2,3-dione and its derivatives.

Post-crosslinking is typically carried out by spraying a solution of the post-crosslinker onto the base polymer or the dry base-polymeric particles. Spraying is followed by thermal drying, and the post-crosslinking reaction can take place not only before but also during drying.

Preferred post-crosslinkers v) are amide acetals or carbamic esters of the general formula I

(I)

where
$R^1$ is $C_1$-$C_{12}$-alkyl, $C_2$-$C_{12}$-hydroxyalkyl, $C_2$-$C_{12}$-alkenyl or $C_6$-$C_{12}$-aryl,
$R^2$ is X or $OR^6$,
$R^3$ is hydrogen, $C_1$-$C_{12}$-alkyl, $C_2$-$C_{12}$-hydroxyalkyl, $C_2$-$C_{12}$-alkenyl or $C_6$-$C_{12}$-aryl, or X,
$R^4$ is $C_1$-$C_{12}$-alkyl, $C_2$-$C_{12}$-hydroxyalkyl, $C_2$-$C_{12}$-alkenyl or $C_6$-$C_{12}$-aryl,
$R^5$ is hydrogen, $C_1$-$C_{12}$-alkyl, $C_2$-$C_{12}$-hydroxyalkyl, $C_2$-$C_{12}$-alkenyl, $C_1$-$C_{12}$-acyl or $C_6$-$C_{12}$-aryl,
$R^6$ is $C_1$-$C_{12}$-alkyl, $C_2$-$C_{12}$-hydroxyalkyl, $C_2$-$C_{12}$-alkenyl, $C_1$-$C_{12}$-acyl or $C_6$-$C_{12}$-aryl and
X is a carbonyl oxygen common to $R^2$ and $R^3$,
wherein $R^1$ and $R^4$ and/or $R^5$ and $R^6$ can be a bridged $C_2$-$C_6$-alkanediyl and wherein the above mentioned radicals $R^1$ to $R^6$ can still have in total one to two free valences and can be attached through these free valences to at least one suitable basic structure, for example 2-oxazolidones, such as 2-oxazolidone and N-hydroxyethyl-2-oxazolidone, N-hydroxypropyl-2-oxazolidone, N-methyl-2-oxazolidone, N-acyl-2-oxazolidones, such as N-acetyl-2-oxazolidone, 2-oxotetrahydro-1,3-oxazine, bicyclic amide acetals, such as 5-methyl-1-aza-4,6-dioxabicyclo[3.3.0]octane, 1-aza-4,6-dioxabicyclo[3.3.0]octane and 5-isopropyl-1-aza-4,6-dioxabicyclo[3.3.0]octane, bis-2-oxazolidones and poly-2-oxazolidones;
or:
polyhydric alcohols, in which case the molecular weight of the polyhydric alcohol is preferably less than 100 g/mol, preferably less than 90 g/mol, more preferably less than 80 g/mol and most preferably less than 70 g/mol per hydroxyl group and the polyhydric alcohol has no vicinal, geminal, secondary or tertiary hydroxyl groups, and polyhydric alcohols are either diols of the general formula IIa

(IIa)

where $R^6$ is either an unbranched dialkyl radical of the formula —$(CH_2)_m$—, where m is an integer from 3 to 20 and preferably from 3 to 12, and both the hydroxyl groups are terminal, or an unbranched, branched or cyclic dialkyl radical or polyols of the general formula Ith

(IIb)

where $R^7$, $R^8$, $R^9$ and $R^{10}$ are independently hydrogen, hydroxyl, hydroxymethyl, hydroxyethyloxymethyl, 1-hydroxyprop-2-yloxymethyl, 2-hydroxypropyloxymethyl, methyl, ethyl, n-propyl, isopropyl, n-butyl, n-pentyl, n-hexyl, 1,2-dihydroxyethyl, 2-hydroxyethyl, 3-hydroxypropyl or 4-hydroxybutyl and in total 2, 3 or 4 and preferably 2 or 3 hydroxyl groups are present, and not more than one of $R^7$, $R^8$, $R^9$ and $R^{10}$ is hydroxyl, examples being 1,3-propanediol, 1,5-pentanediol, 1,6-hexanediol and 1,7-heptanediol, 1,3-butanediol, 1,8-octanediol, 1,9-nonanediol and 1,10-decanediol, butane-1,2,3-triol, butane-1,2,4-triol, glycerol, trimethylolpropane, trimethylolethane, pentaerythritol, glycerol each having 1 to 3 ethylene oxide units per molecule, trimethylolethane or trimethylolpropane each having 1 to 3 ethylene oxide units per molecule, propoxylated glycerol, trimethylolethane or trimethylolpropane each having 1 to 3 propylene oxide units per molecule, 2-tuply ethoxylated or propoxylated neopentylglycol,
or cyclic carbonates of the general formula III (III)

where $R^{11}$, $R^{12}$, $R^{13}$, $R^{14}$, $R^{15}$ and $R^{16}$ are independently hydrogen, methyl, ethyl, n-propyl, isopropyl, n-butyl, sec-butyl or isobutyl, and n is either 0 or 1, examples being ethylene carbonate and propylene carbonate,
or bisoxazolines of the general formula IV (IV)

where $R^{17}$, $R^{18}$, $R^{19}$, $R^{20}$, $R^{21}$, $R^{22}$, $R^{23}$ and $R^{24}$ are independently hydrogen, methyl, ethyl, n-propyl, isopropyl, n-butyl, sec-butyl or isobutyl and $R^{25}$ is a single bond, a linear, branched or cyclic $C_1$-$C_{12}$-dialkyl radical or polyalkoxydiyl radical which is constructed of one to ten ethylene oxide and/or propylene oxide units, and is comprised of polyglycol dicarboxylic acids for example. An example for a compound under formula IV being 2,2'-bis(2-oxazoline).

The at least one post-crosslinker v) is typically used in an amount of about 1.50 wt. % or less, preferably not more than 0.50% by weight, more preferably not more than 0.30% by weight and most preferably in the range from 0.001% and 0.15% by weight, all percentages being based on the base polymer, as an aqueous solution. It is possible to use a single post-crosslinker v) from the above selection or any desired mixtures of various post-crosslinkers.

The aqueous post-crosslinking solution, as well as the at least one post-crosslinker v), can typically further comprise a cosolvent. Cosolvents which are technically highly useful are $C_1$-$C_6$-alcohols, such as methanol, ethanol, n-propanol, isopropanol, n-butanol, sec-butanol, tert-butanol or 2-methyl-1-propanol, $C_2$-$C_5$-diols, such as ethylene glycol, 1,2-propylene glycol, 1,3-propanediol or 1,4-butanediol, ketones, such as acetone, or carboxylic esters, such as ethyl acetate.

A preferred embodiment does not utilize any cosolvent. The at least one post-crosslinker v) is then only employed as a solution in water, with or without an added deagglomerating aid. Deagglomerating aids are known to one skilled in the art and are described for example in DE-A-10 239 074 and WO 2006/042704, which are each hereby expressly incorporated herein by reference. Preferred deagglomerating aids are surfactants such as ethoxylated and alkoxylated derivatives of 2-propylheptanol and also sorbitan monoesters. Particularly preferred deagglomerating aids are polyoxyethylene 20 sorbitan monolaurate and polyethylene glycol 400 monostearate.

The concentration of the at least one post-crosslinker v) in the aqueous post-crosslinking solution is for example in the range from 1% to 50% by weight, preferably in the range from 1.5% to 20% by weight and more preferably in the range from 2% to 5% by weight, based on the post-crosslinking solution.

In a further embodiment, the post-crosslinker is dissolved in at least one organic solvent and spray dispensed; in this case, the water content of the solution is less than 10 wt. %, preferably no water at all is utilized in the post-crosslinking solution.

It is, however, understood that post-crosslinkers which effect comparable surface-crosslinking results with respect to the final polymer performance may of course be used in this invention even when the water content of the solution containing such post-crosslinker and optionally a cosolvent is anywhere in the range of >0 to <100% by weight.

The total amount of post-crosslinking solution based on the base polymer is typically in the range from 0.3% to 15% by weight and preferably in the range from 2% to 6% by weight. The practice of post-crosslinking is common knowledge to those skilled in the art and described for example in DE-A-12 239 074 and WO 2006/042704.

Spray nozzles useful for post-crosslinking are not subject to any restriction. Suitable nozzles and atomizing systems are described for example in the following literature references: Zerstäuben von Flüssigkeiten, Expert-Verlag, volume 660, Reihe Kontakt & Studium, Thomas Richter (2004) and also in Zerstäubungstechnik, Springer-Verlag, VDI-Reihe, Günter Wozniak (2002). Mono- and polydisperse spraying systems can be used. Suitable polydisperse systems include one-material pressure nozzles (forming a jet or lamellae), rotary atomizers, two-material atomizers, ultrasonic atomizers and impact nozzles.

The spraying with the solution of post-crosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Useful mixers include for example Lödige® mixers, Bepex® mixers, Nauta® mixers, Processall® mixers and Schugi® mixers.

After spraying, the water-absorbing polymeric particles are thermally dried, and the post-crosslinking reaction can take place before, during or after drying.

It is particularly preferable to utilize a fluidized bed dryer for the crosslinking reaction, and the residence time is then preferably below 30 minutes, more preferably below 20 minutes and most preferably below 10 minutes.

To produce a very white polymer, the gas space in the dryer is kept as free as possible of oxidizing gases; at any rate, the volume fraction of oxygen in the gas space is not more than 14% by volume.

The water-absorbing polymeric particles can have a particle size distribution in the range from 45 µm to 4000 µm. Particle sizes used in the hygiene sector preferably range from 45 µm to 1000 µm, preferably from 45-850 µm, and especially from 100 µm to 850 µm. It is preferable to coat water-absorbing polymeric particles having a narrow particle size distribution, especially 100-850 µm, or even 100-600 µm.

Narrow particle size distributions are those in which not less than 80% by weight of the particles, preferably not less than 90% by weight of the particles and most preferably not less than 95% by weight of the particles are within the selected range; this fraction can be determined using the familiar sieve method of EDANA 420.2-02 "Particle Size Distribution". Selectively, optical methods can be used as well, provided these are calibrated against the accepted sieve method of EDANA.

Preferred narrow particle size distributions have a span of not more than 700 µm, more preferably of not more than 600 µm, and most preferably of less than 400 µm. Span here refers to the difference between the coarse sieve and the fine sieve which bound the distribution. The coarse sieve is not coarser than 850 µm and the fine sieve is not finer than 45 µm. Particle size ranges which are preferred for the purposes of the present invention are for example fractions of 150-600 µm (span: 450 µm), of 200-700 µm (span: 500 µm), of 150-500 µm (span: 350 µm), of 150-300 µm (span: 150 µm), of 300-700 µm (span: 400 µm), of 400-800 µm (span: 400 µm), of 100-800 µm (span: 700 µm).

Preference is likewise given to monodisperse water-absorbing polymeric particles as obtained from the inverse suspension polymerization process. It is similarly possible to select mixtures of monodisperse particles of different diameter as water-absorbing polymeric particles, for example mixtures of monodisperse particles having a small diameter and monodisperse particles having a large diameter. It is similarly possible to use mixtures of monodisperse with polydisperse water-absorbing polymeric particles.

Coating these water-absorbing polymeric particles having narrow particle size distributions and preferably having a maximum particle size of <600 µm according to the present invention provides a water-absorbing material, which swells rapidly and therefore is particularly preferred.

The water-absorbing particles can be spherical in shape as well as irregularly shaped particles.

Polyurethane Polymers for Coating

The polyurethanes to be used for coating herein are film forming and have elastomeric properties. They are disclosed in WO 2006/082239 the disclosure of which is incorporated herein in its entirety.

Film forming means that the polyurethane (PU) polymer can readily be made into a layer or coating upon evaporation of the solvent in which it is dissolved or dispersed. The polymer may for example be thermoplastic and/or crosslinked. Elastomeric means the material will exhibit stress induced deformation that is partially or completely reversed upon removal of the stress.

In one embodiment, the PU polymer has a tensile stress at break in the wet state of at least 1 MPa, or even at least 3 MPa and more preferably at least 5 MPa, or even at least 8 MPa. Most preferred materials have tensile stress at break in the wet state of at least 10 MPa, preferably at least 40 MPa. This can be determined by the test method, described below.

In one embodiment, particularly preferred PU polymers herein are materials that have a wet secant elastic modulus at 400% elongation ($SM_{wet\ 400\%}$) of at least 0.25 MPa, preferably at least about 0.50 MPa, more preferably at least about 0.75 or even at least 2.0 MPa, and most preferably of at least about 3.0 MPa as determined by the test method below.

In one embodiment, preferred PU polymers herein have a ratio of [wet secant elastic modulus at 400% elongation ($SM_{wet\ 400\%}$)] to [dry secant elastic modulus at 400% elongation ($SM_{dry\ 400\%}$)] of 10 or less, preferably of 1.4 or less, more preferably 1.2 or less or even more preferably 1.0 or less, and it may be preferred that this ratio is at least 0.1, preferably at least 0.6, or even at least 0.7.

In one embodiment, the PU polymer is present in the form of a coating that has a shell tension, which is defined as the (theoretical equivalent shell caliper)×(average wet secant elastic modulus at 400% elongation) of about 5 to 200 N/m, or preferably of 10 to 170 N/m, or more preferably 20 to 130 N/m, and even more preferably 40 to 110 N/m.

In one embodiment of the invention where the water-absorbing polymer particles herein have been surface-crosslinked (either prior to application of the shell described herein, or at the same time as applying said shell), it may even be more preferred that the shell tension of the water-absorbing material is in the range from 15 N/m to 60 N/m, or even more preferably from 20 N/m to 60 N/m, or preferably from 40 to 60 N/m.

In yet another embodiment wherein the water absorbing polymeric particles are not surface crosslinked, it is even more preferred that the shell tension of the water-absorbing material is in the range from about 60 to 110 N/m.

In one embodiment, the PU polymer is present in the form of a coating on the surface of the water absorbing material, that has a shell impact parameter, which is defined as the (average wet secant elastic modulus at 400% elongation)*(relative Weight of the shell polymer compared to the total weight of the coated polymer) of about 0.03 MPa to 0.6 MPa, preferably 0.07 MPa to 0.45 MPa, more preferably about 0.1 to 0.35 MPa. The "relative weight of the shell polymer compared to the total weight of the coated polymer" is a fraction typically between 0.0 to 1.0.

The polymers polyurethanes, in contrast to the water-absorbing polymeric particles, swell typically only little if at all on contact with aqueous fluids. This means in practice that the film-forming polymers have preferably a water-swelling capacity of less than 1 g/g, or even less than 0.5 g/g, or even less than 0.2 g/g or even less than 0.1 g/g, as may be determined by the method, as set out below.

The PU polymer is typically such that the resulting coating on the water-swellable polymers herein is not water-soluble and, preferably not water-dispersible.

In order to impart desirable properties to the elastic polymer, additionally fillers such as particulates, oils, solvents, plasticizers, surfactants, dispersants may be optionally incorporated.

The mechanical properties as described above are believed to be characteristic in certain embodiments for a suitable PU polymer for coating. The polymer may be hydrophobic or hydrophilic. For fast wetting it is however preferable that the polymer is also hydrophilic.

The PU polymer can for example be applied from a solution or an aqueous solution or in another embodiment can be applied from a dispersion or in a preferred embodiment from an aqueous dispersion. The solution can be prepared using any suitable organic solvent for example acetone, isopropanol, tetrahydrofuran, methyl ethyl ketone, dimethyl sulfoxide, dimethylformamide, chloroform, ethanol, methanol and mixtures thereof.

Suitable elastomeric polymers which are applicable from solution are for example Estane® 58245 (Noveon, Cleveland, USA), Estane® 4988, Estane® 4986, Estane® X-1007, Estane® T5410, Irogran® PS370-201 (Huntsman Polyurethanes), Irogran® VP 654/5, Elastollan® LP 9109 (Elastogran) or Astacin® Finish products (BASF SE), in particular Astacin® Finish PUMN TF.

In a preferred embodiment the polyurethane is in the form of an aqueous dispersion.

The synthesis of polyurethanes and the preparation of polyurethane dispersions is well described for example in Ullmanns Encyclopedia of Industrial Chemistry, Sixth Edition, 2000 Electronic Release.

In one embodiment, the hydrophilic properties are achieved as a result of the polyurethane comprising hydrophilic polymer blocks, for example polyether groups having a fraction of groups derived from ethylene glycol ($CH_2CH_2O$) or from 1,4-butanediol ($CH_2CH_2CH_2CH_2O$) or from propylene glycol ($CH_2CH_2CH_2O$), or mixtures thereof. Polyether-polyurethanes are therefore preferred film-forming polymers. The hydrophilic blocks can be constructed in the manner of comb polymers where parts of the side chains or all side chains are hydrophilic polymeric blocks. But the hydrophilic blocks can also be constituents of the main chain (i.e., of the polymer's backbone). A preferred embodiment utilizes polyurethanes where at least the predominant fraction of the hydrophilic polymeric blocks is present in the form of side chains. The side chains can in turn be block copolymers such as poly(ethylene glycol)-co-polypropylene glycol).

It is further possible to obtain hydrophilic properties for the polyurethanes through an elevated fraction of ionic groups, preferably carboxylate, sulfonate, phosphonate or ammonium groups. The ammonium groups may be protonated or alkylated tertiary or quarternary groups. Carboxylates, sulfonates, and phosphates may be present as alkali-metal or ammonium salts. Suitable ionic groups and their respective precursors are for example described in "Ullmanns Encyclopädie der technischen Chemie", $4^{th}$ Edition, Volume 19, p. 311-313 and are furthermore described in DE-A 1 495 745 and WO 03/050156.

It is well understood by those skilled in the art that polyurethanes also include allophanate, biuret, carbodiimide, oxazolidinyl, isocyanurate, uretdione, and other linkages in addition to urethane and urea linkages.

In one embodiment the block copolymers useful herein are preferably polyether urethanes and polyester urethanes. Especially preferred are polyether urethanes comprising polyalkylene glycol units, especially polyethylene glycol units or poly(tetramethylene glycol) units.

As used herein, the term "alkylene glycol" includes both alkylene glycols and substituted alkylene glycols having 2 to 10 carbon atoms, such as ethylene glycol, 1,3-propylene glycol, 1,2-propylene glycol, 1,2-butylene glycol, 1,3-butylene glycol, 1,4-butylene glycol, styrene glycol and the like.

The polyurethanes used according to the present invention are generally obtained by reaction of polyisocyanates with active hydrogen-containing compounds having two or more reactive groups. These include
a) high molecular weight compounds having a molecular weight in the range of preferably 300 to 100 000 g/mol especially from 500 to 30 000 g/mol
b) low molecular weight compounds and
c) compounds having polyether groups, especially polyethylene oxide groups or polytetrahydrofuran groups and a molecular weight in the range from 200 to 20 000 g/mol, the polyether groups in turn having no reactive groups.

These compounds can also be used as mixtures.

Suitable polyisocyanates have an average of about two or more isocyanate groups, preferably an average of about two to about four isocyanate groups and include aliphatic, cycloaliphatic, araliphatic, and aromatic polyisocyanates, used alone or in mixtures of two or more. Diisocyanates are more preferred. Especially preferred are aliphatic and cycloaliphatic polyisocyanates, especially diisocyanates.

Specific examples of suitable aliphatic diisocyanates include alpha, omega-alkylene diisocyanates having from 5 to 20 carbon atoms, such as hexamethylene-1,6-diisocyanate, 1,12-dodecane diisocyanate, 2,2,4-trimethylhexamethylene diisocyanate, 2,4,4-trimethyl-hexamethylene diisocyanate, 2-methyl-1,5-pentamethylene diisocyanate, and the like. Polyisocyanates having fewer than 5 carbon atoms can be used but are less preferred because of their high volatility and toxicity. Preferred ali-phatic polyisocyanates include hexamethylene-1,6-diisocyanate, 2,2,4-trimethyl-hexamethylene diisocyanate, and 2,4,4-trimethyl-hexamethylene diisocyanate.

Specific examples of suitable cycloaliphatic diisocyanates include dicyclohexylmethane diisocyanate, (commercially available as Desmodur® W from Bayer Corporation), isophorone diisocyanate, 1,4-cyclohexane diisocyanate, 1,3-bis (isocyanatomethyl)cyclohexane, and the like. Preferred cycloaliphatic diisocyanates include dicyclohexylmethane diisocyanate and isophorone diisocyanate.

Specific examples of suitable araliphatic diisocyanates include m-tetramethyl xylylene diisocyanate, p-tetramethyl xylylene diisocyanate, 1,4-xylylene diisocyanate, 1,3-xylylene diisocyanate, and the like. A preferred araliphatic diisocyanate is tetramethyl xylylene diisocyanate.

Examples of suitable aromatic diisocyanates include 4,4'-diphenylmethane diisocyanate, toluene diisocyanate, their isomers, naphthalene diisocyanate, and the like. A preferred aromatic diisocyanate is toluene diisocyanate and 4,4'-diphenylmethane diisocyanate.

Examples of high molecular weight compounds a) having 2 or more reactive groups are such as polyester polyols and polyether polyols, as well as polyhydroxy polyester amides, hydroxyl-containing polycaprolactones, hydroxyl-containing acrylic copolymers, hydroxyl-containing epoxides, polyhydroxy polycarbonates, polyhydroxy polyacetals, polyhydroxy polythioethers, polysiloxane polyols, ethoxylated polysiloxane polyols, polybutadiene polyols and hydrogenated polybutadiene polyols, polyacrylate polyols, halogenated polyesters and polyethers, and the like, and mixtures thereof. The polyester polyols, polyether polyols, polycarbonate polyols, polysiloxane polyols, and ethoxylated polysiloxane polyols are preferred. Particular preference is given to polyesterpolyols, polycarbonate polyols and polyalkylene ether polyols and in particular to polyesterpolyols. The number of functional groups in the aforementioned high molecular weight compounds is preferably on average in the range from 1.8 to 3 and especially in the range from 2 to 2.2 functional groups per molecule.

The polyester polyols typically are esterification products prepared by the reaction of organic polycarboxylic acids or their anhydrides with a stoichiometric excess of a diol.

The diols used in making the polyester polyols include alkylene glycols, e.g., ethylene glycol, 1,2- and 1,3-propylene glycols, 1,2-, 1,3-, 1,4-, and 2,3-butane diols, hexane diols, neopentyl glycol, 1,6-hexanediol, 1,8-octanediol, and other glycols such as bisphenol-A, cyclohexanediol, cyclohexane dimethanol (1,4-bis-hydroxymethylcycohexane), 2-methyl-1,3-propanediol, 2,2,4-trimethyl-1,3-pentanediol, diethylene glycol, triethylene glycol, tetraethylene glycol, polyethylene glycol, dipropylene glycol, polypropylene glycol, dibutylene glycol, polybutylene glycol, dimerate diol, hydroxylated bisphenols, polyether glycols, halogenated diols, and the like, and mixtures thereof. Preferred diols include ethylene glycol, diethylene glycol, butane diol, hexane diol, and neopentylglycol. Alternatively or in addition, the equivalent mercapto compounds may also be used.

Suitable carboxylic acids used in making the polyester polyols include dicarboxylic acids and tricarboxylic acids and anhydrides, e.g., maleic acid, maleic anhydride, succinic acid, glutaric acid, glutaric anhydride, adipic acid, suberic acid, pimelic acid, azelaic acid, sebacic acid, chlorendic acid, 1,2,4-butane-tricarboxylic acid, o-phthalic acid, the isomers of phthalic acid, phthalic anhydride, fumaric acid, dimeric fatty acids made from oleic acid, and the like, and mixtures thereof. Preferred polycarboxylic acids used in making the polyester polyols include aliphatic or aromatic dibasic acids.

Examples of suitable polyester polyols include poly(glycol adipate)s, poly(ethylene terephthalate) polyols, polycaprolactone polyols, orthophthalic polyols, sulfonated and phosphonated polyols, and the like, and mixtures thereof.

The preferred polyester polyol is a diol. Preferred polyester diols include poly(butanediol adipate); hexanediol adipic acid and isophthalic acid polyesters such as hexaneadipate isophthalate polyester; hexanediol neopentyl glycol adipic acid polyester diols, e.g., Piothane 67-3000 HNA (Panolam Industries) and Piothane 67-1000 HNA, as well as propylene glycol maleic anhydride adipic acid polyester diols, e.g., Piothane SO-1000 PMA, and hexane diol neopentyl glycol fumaric acid polyester diols, e.g., Piothane 67-SO0 HNF. Other preferred Polyester diols include Rucoflex® S101.5-3.5, S1040-3.5, and S-1040-110 (Bayer Corporation).

Polyether polyols are obtained in known manner by the reaction of a starting compound that contain reactive hydrogen atoms, such as water or the diols set forth for preparing the polyester polyols, and alkylene glycols or cyclic ethers, such as ethylene glycol, propylene glycol, butylene glycol, styrene glycol, ethylene oxide, propylene oxide, 1,2-butylene oxide, 2,3-butylene oxide, oxetane, tetrahydrofuran, epichlorohydrin, and the like, and mixtures thereof. Preferred polyethers include poly(ethylene glycol), polypropylene glycol), polytetrahydrofuran, and co[poly(ethylene glycol)-polypropylene glycol)]. Polyethylenglycol and Polypropyleneglycol can be used as such or as physical blends. In case that propyleneoxide and ethylenoxide are copolymerized, these polypropylene-co-polyethylene polymers can be used as random polymers or block-copolymers.

In one embodiment the polyetherpolyol is a constituent of the main polymer chain.

In another embodiment the polyetherol is a terminal group of the main polymer chain.

In yet another embodiment the polyetherpolyol is a constituent of a side chain which is comb-like attached to the main chain. An example of such a monomer is Tegomer D-3403 (Degussa).

Polycarbonates include those obtained from the reaction of diols such 1,3-propanediol, 1,4-butanediol, 1,6-hexanediol, diethylene glycol, triethylene glycol, tetraethylene glycol, and the like, and mixtures thereof with dialkyl carbonates such as diethyl carbonate, diaryl carbonates such as diphenyl carbonate or phosgene.

Examples of low molecular weight compounds b) having two reactive functional groups are the diols such as alkylene glycols and other diols mentioned above in connection with the preparation of polyesterpolyols. They also include diamines such as diamines and polyamines which are among the preferred compounds useful in preparing the aforesaid polyesteramides and polyamides. Suitable diamines and polyamines include 1,2-diaminoethane, 1,6-diaminohexane, 2-methyl-1,5-pentanediamine, 2,2,4-trimethyl-1,6-hexanediamine, 1,12-diaminododecane, 2-aminoethanol, 2-[(2-aminoethyl)amino]-ethanol, piperazine, 2,5-dimethylpiperazine, 1-amino-3-aminomethyl-3,5,5-trimethylcyclohexane (isophorone diamine or IPDA), bis-(4-aminocyclohexyl)- methane, bis-(4-amino-3-methyl-cyclohexyl)-methane, 1,4-diaminocyclohexane, 1,2-propylenediamine, hydrazine, urea, amino acid hydrazides, hydrazides of semicarbazidocarboxylic acids, bis-hydrazides and bis-semicarbazides, diethylene triamine, triethylene tetramine, tetraethylene pentamine, pentaethylene hexamine, N,N,N-tris-(2-aminoethyl)amine, N-(2-piperazinoethyl)-ethylene diamine, N,N'-bis-(2-aminoethyl)-piperazine, N,N,N'-tris-(2-aminoethyl)ethylene diamine, N—[N-(2-aminoethyl)-2-aminoethyl]-N'-(2-aminoethyl)-piperazine, N-(2-amino ethyl)-N'-(2-piperazinoethyl)-ethylene diamine, N,N-bis-(2-aminoethyl)-N-(2-piperazinoethyl)amine, N,N-bis-(2-piperazinoethyl)amine, polyethylene imines, iminobispropylamine, guanidine, melamine, N-(2-aminoethyl)-1,3-propane diamine, 3,3'-diaminobenzidine, 2,4,6-triaminopyrimidine, polyoxypropylene amines, tetrapropylene-pentamine, tripropylenetetramine, N,N-bis-(6-aminohexyl)amine, N,N'-bis-(3-aminopropyl)ethylene diamine, and 2,4-bis-(4'-aminobenzyl)-aniline, and the like, and mixtures thereof. Preferred diamines and polyamines include 1-amino-3-aminomethyl-3,5,5-trimethyl-cyclohexane (isophorone diamine or IPDA), bis-(4-aminocyclohexyl)-methane, bis-(4-amino-3-methylcyclohexyl)-methane, ethylene diamine, diethylene triamine, triethylene tetramine, tetraethylene pentamine, and pentaethylene hexamine, and the like, and mixtures thereof. Other suitable diamines and polyamines for example include Jeffamine® D-2000 and D-4000, which are amine-terminated polypropylene glycols differing only by molecular weight, and Jeffamine® XTJ-502, T 403, T 5000, and T 3000 which are amine terminated polyethyleneglycols, amine terminated co-polypropylene-polyethylene glycols, and triamines based on propoxylated glycerol or trimethylolpropane and which are available from Huntsman Chemical Company.

The polyurethane may additionally contain functional groups which can undergo further crosslinking reactions and which can optionally render them self-crosslinkable.

Compounds having at least one additional crosslinkable functional group include those having carboxylic, carbonyl, amine, hydroxyl, and hydrazide groups, and the like, and mixtures of such groups. The typical amount of such optional compound is up to about 1 milliequivalent, preferably from about 0.05 to about 0.5 milliequivalent, and more preferably from about 0.1 to about 0.3 milliequivalent per gram of final polyurethane on a dry weight basis.

The preferred compounds for incorporation of carboxylic groups into the isocyanate-terminated prepolymer are hydroxy-carboxylic acids having the general formula $(HO)_xQ(COOH)_y$ wherein Q is a straight or branched hydrocarbon radical having 1 to 12 carbon atoms, and x and y are 1 to 3. Examples of such hydroxy-carboxylic acids include citric acid, dimethylolpro-panoic acid (DMPA), dimethylol butanoic acid (DMBA), glycolic acid, lactic acid, malic acid, dihydroxy-maleic acid, tartaric acid, hydroxypivalic acid, and the like, and mixtures thereof. Dihydroxy-carboxylic acids are more preferred with dimethylolpropanoic acid (DMPA) being most preferred.

Other suitable compounds providing crosslinkability include thioglycolic acid, 2,6-dihydroxybenzoic acid, and the like, and mixtures thereof.

Optional neutralization of the prepolymer having pendant carboxyl groups converts the carboxyl groups to carboxylate anions, thus having a water-dispersibility enhancing effect. Suitable neutralizing agents include tertiary amines, metal hydroxides, ammonia, and other agents well known to those skilled in the art.

As a chain extender, at least one of water, an inorganic or organic polyamine having an average of about 2 or more primary and/or secondary amine groups, polyalcohols, ureas, or combinations thereof is suitable for use in the present invention. Suitable organic amines for use as a chain extender include diethylene triamine (DETA), ethylene diamine (EDA), meta-xylylenediamine (MXDA), aminoethyl ethanolamine (AEEA), 2-methyl pentane diamine, and the like, and mixtures thereof. Also suitable for practice in the present invention are propylene diamine, butylene diamine, hexamethylene diamine, cyclohexylene diamine, phenylene diamine, tolylene diamine, 3,3-dichlorobenzidene, 4,4'-methylene-bis-(2-chloroaniline), 3,3-dichloro-4,4-diamino diphenylmethane, sulfonated primary and/or secondary amines, and the like, and mixtures thereof. Suitable inorganic and organic amines include hydrazine, substituted hydrazines, and hydrazine reaction products, and the like, and mixtures thereof. Suitable polyalcohols include those having from 2 to 12 carbon atoms, preferably from 2 to 8 carbon atoms, such as ethylene glycol, diethylene glycol, neopentyl glycol, butanediols, hexanediol, and the like, and mixtures thereof. Suitable ureas include urea and its derivatives, and the like, and mixtures thereof. Hydrazine is preferred and is most preferably used as a solution in water. The amount of chain extender typically ranges from about 0.5 to about 0.95 equivalents based on available isocyanate.

Preferred aqueous polyurethane dispersions are Hauthane® HD-4638 (ex Hauthaway), Hydrolar® HC 269 (ex Colm, Italy), Impraperm® 48180 (ex Bayer Material Science AG, Germany), Lurapret® DPS (ex BASF Germany), Permax®120, Permax® 200, and Permax® 220 (ex Noveon, Brecksville, Ohio),), Syntegra® YM2000 and Syntegra® YM2100 (ex Dow, Midland, Mich.) Witcobond G-213, Witcobond G-506, Witcobond G-507, Witcobond® 736 (ex Uniroyal Chemical, Middlebury, Conn.) and Astacin® Finish products, in particular Astacin® Finish PUMN TF (ex BASF Germany).

Particularly suitable elastic film-forming polyurethanes are extensively described in the literature references hereinbelow and expressly form part of the subject matter of the present disclosure. Particularly hydrophilic thermoplastic polyurethanes are sold by Noveon, Brecksville, Ohio, under the tradenames of Permax® 120, Permax 200 and Permax 220 and are described in detail in "Proceedings International Waterborne High Solids Coatings, 32, 299, 2004" and were presented to the public in February 2004 at the "International Waterborne, High-Solids, and Powder Coatings Symposium" in New Orleans, USA. The preparation is described in detail in US 2003/0195293. Furthermore, the polyurethanes described in U.S. Pat. No. 4,190,566, U.S. Pat. No. 4,092,286, US 2004/0214937 and also WO 03/050156 expressly form part of the subject matter of the present disclosure.

More particularly, the polyurethanes described can be used in mixtures with each other or with other film-forming polymers, fillers, oils, water-soluble polymers or plasticizing agents in order that particularly advantageous properties may be achieved with regard to hydrophilicity, water perviousness and mechanical properties.

The PU polymers are preferably applied in an amount of 0.1-25 parts by weight of the film-forming polymer (reckoned as solids material) to 100 parts by weight of dry water-absorbing polymeric particles. The amount of PU polymer used per 100 parts by weight of water-absorbing polymeric particles is preferably 0.1-15 parts by weight, especially 0.5-10 parts by weight, more preferably 0.5-7 parts by weight, even more preferably 0.5-5 parts by weight and in particular 0.5-4.5 parts by weight, 0.5-4 parts by weight or 0.5-3 parts by weight with an amount of 0.5-2.5 parts by weight and in particular 1-2 parts by weight being particularly preferred.

The polyurethane can be as a hotmelt, as a dispersion, as an aqueous dispersion, as an aqueous solution or as an organic solution to the particles of the water-absorbing addition polymer. The form in which the film-forming polymer, especially the polyurethane is applied to the water-absorbing polymeric particles is preferably as a solution or more preferably as an aqueous dispersion.

Useful solvents for polyurethanes include solvents which make it possible to establish 1 to not less than 40% by weight concentrations of the polyurethane in the respective solvent or mixture. As examples there may be mentioned alcohols, esters, ethers, ketones, amides, and halogenated hydrocarbons like methyl ethyl ketone, acetone, isopropanol, tetrahydrofuran, dimethylformamide, chloroform and mixtures thereof. Solvents which are polar, aprotic and boil below 100° C. at ambient pressure are particularly advantageous.

Aqueous herein refers to water and also mixtures of water with up to 20% by weight of water-miscible solvents, based on the total amount of solvent. Water-miscible solvents are miscible with water in the desired use amount at 25° C. and 1 bar. They include alcohols such as methanol, ethanol, propanol, isopropanol, ethylene glycol, 1,2-propanediol, 1,3-propanediol, ethylene carbonate, glycerol and methoxyethanol and water-soluble ethers such as tetrahydrofuran and dioxane.

It is particularly preferable to effect the coating in a fluidized bed reactor. The water-absorbing particles are introduced as generally customary, depending on the type of the reactor, and are generally coated by spraying with the film-forming polymer as a solid material or preferably as a polymeric solution or dispersion. Aqueous dispersions of the film-forming polymer are particularly preferred for this.

Useful fluidized bed reactors include for example the fluidized or suspended bed coaters familiar in the pharmaceutical industry. Particular preference is given to the Wurster process and the Glatt-Zeller process and these are described for example in "Pharmazeutische Technologie, Georg Thieme Verlag, 2nd edition (1989), pages 412-413" and also in "Arzneiformenlehre, Wissenschaftliche Verlagsbuchandlung mbH, Stuttgart 1985, pages 130-132". Particularly suitable batch and continuous fluidized bed processes on a commercial scale are described in Drying Technology, 20(2), 419-447 (2002).

It is possible that the water-absorbing material comprises two or more layers of coating agent (shells), obtainable by coating the water-absorbing polymers twice or more. This may be the same coating agent or a different coating agent. However, preference for economic reasons is given to a single coating.

The coating may take place at a product and/or carrier gas temperature in the range from 0° C. to 50° C., preferably at 5-45° C., especially 10-40° C. and most preferably 15-35° C.

This may ensure that solvents/liquids used for coating evaporate/and/or that the PU polymers form a annealed film The heat-treating takes place at temperatures above 50° C., preferably in a temperature range from 100 to 200° C., especially 120-160° C. Without wishing to be bound by theory, the heat-treating causes the applied film-forming polyurethane, to flow and form a polymeric film whereby the polymer chains are entangled, so-called annealing. The duration of the heat-treating is dependent on the heat-treating temperature chosen and the glass transition and melting temperatures of the film-forming polymer. In general, a heat-treating time in the range from 30 minutes to 120 minutes will be found to be sufficient. However, the desired formation of the polymeric film can also be achieved when heat-treating for less than 30 minutes, for example in a fluidized bed dryer. Longer times are possible, of course, but especially at higher temperatures can lead to damage in the polymeric film or to the water-absorbing material.

The heat-treating is carried out for example in a downstream fluidized bed dryer, a tunnel dryer, a tray dryer, a tower dryer, one or more heated screws or a disk dryer or a Nara® dryer. Heat-treating is preferably done in a fluidized bed reactor and more preferably directly in the Wurster Coater.

In one embodiment for the process steps of coating, heat-treating, and cooling, it may be possible to use air or dried air in each of these steps.

In other embodiments an inert gas may be used in one or more of these process steps.

In yet another embodiment one can use mixtures of air and inert gas in one or more of these process steps.

The heat-treating is preferably carried out under inert gas. It is particularly preferable that the coating step be carried out under inert gas as well. It is very particularly preferable when the concluding cooling phase is carried out under protective gas too. Preference is therefore given to a process where the production of the water-absorbing material according to the present invention takes place under inert gas.

After the heat-treating step has been concluded, the dried water-absorbing polymeric materials are cooled. To this end, the warm and dry polymer is preferably continuously transferred into a downstream cooler. This can be for example a disk cooler, a Nara paddle cooler or a screw cooler.

The water-absorbing material preferably comprises less than 20% by weight of water, or even less than 10% or even less than 8% or even less than 5%, or even no water. The water content of the water-absorbing material can be determined by the Edana test, number ERT 430.1-99 (February 1999) which involves drying the water-absorbing material at 105° Celsius for 3 hours and determining the moisture content by the weight loss of the water-absorbing materials after drying.

The invention further relates to a water-absorbing polymer material which has a CS-FHA of at least 5 g/g and a FSR of at least 0.17 g/g·s.

According to one embodiment the water-absorbable polymer material has a CS-FHA of at least 8 g/g, in particular at least 10 g/g and a FSR of at least 0.19 g/g·s, in particular at least 0.20 g/g·s.

The water-absorbable polymer material as mentioned before preferably has in addition a core shell saline flow conductivity (CS-SFC) of at least $100 \cdot 10^{-7}$ cm$^3$s/g, in particular of at least $150 \cdot 10^{-7}$ cm$^3$s/g, more preferably at least $200 \cdot 10^{-7}$ cm$^3$s/g and especially preferred at least $250 \cdot 10^{-7}$ cm$^3$s/g.

According to another embodiment the water-absorbable polymer material which has a CS-FHA of at least 5 g/g and a FSR of at least 0.17 g/g·s and optionally a core shell saline flow conductivity (CS-SFC) of at least $100 \cdot 10^{-7}$ cm$^3$s/g is obtainable according to the process of the invention.

The water-absorbing material of the present invention is notable for the fact that the particles, which have an irregular shape when dry, assume in the swollen state a more rounded shape/morphology, since the swelling of the absorbent core is distributed via the rebound forces of the elastic polymeric envelope over the surface and the elastic polymeric envelope substantially retains its properties in this respect during the swelling process and in use. The enveloping film-forming polyurethane is permeable to saline, so that the polymer particles achieve excellent absorption values in the CS-CRC (Core Shell Centrifugation Retention Capacity) test and also good permeability in the CS-SFC test.

In addition, the water-absorbing materials of the invention have a high permeability for liquid flow through the gel bed as can be measured with the CS-SFC test set out herein.

Absorbent Structures and Absorbent Articles

The absorbent structures herein may be any three-dimensional structure suitable for absorption and retention of fluids. In some embodiments, the absorbent structure may be a structure suitable for absorption of bodily fluids, such as urine or blood. For example the absorbent structure may be part of, or may be, the absorbent core of an absorbent article, such as a hygiene article selected from panty-liners, sanitary napkins and absorbent pads, absorbent inserts, and in particular diapers, including adult and infant diapers and including pant-type diapers and diapers with fasteners, and diaper liners and diaper holders.

"Diaper" refers to an absorbent article generally worn by infants and adult incontinent persons about the lower torso.

The absorbent structure typically comprises the water-absorbing material described herein and a structuring material, and a support layer(s). The absorbent structure may be the storage layer of an absorbent article, such as a diaper, or the acquisition layer, or both, either as two or more layers or as unitary structure.

The support layer (s) may be foam, film, woven web and/or nonwoven web, as known in the art, including spunbond, meltblown and/or carded nonwovens and laminates thereof. One preferred material is a so-called nonwoven laminates material, one or more melt-blown between two or more spunbonded layer. Preferred non-woven materials are provided from synthetic fibers, such as PE, PET and most preferably PP.

The absorbent structure may also comprise a structuring agent, such as absorbent fibrous material, such as absorbent cellulose fibers, and/or an adhesive, for example a fibrous adhesive, and/or thermoplastic fibrous material, which each may serve to immobilize the water-absorbent material. It may be preferred in some embodiments that said absorbent structure herein comprises large amounts of the water-absorbing material herein and only very little or no absorbent cellulose fibers, preferably less than 10% by weight of the water-absorbent material herein, or preferably even less than 5% by weight.

Preferred absorbent structures herein comprise a layer of a support material, and thereon a layer of particulate water-absorbing material (as described herein), optionally as a discontinuous layer, and thereon a layer of an adhesive or thermoplastic material or preferably a thermoplastic adhesive material, e.g. in the form of fibers, which is applied onto the layer of said water-absorbing polymeric particulate material.

The thermoplastic adhesive may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic composition may be a hot melt adhesive comprising at least one thermoplastic polymer in combination with other thermoplastic diluents such as tackifying resins, plasticizers and additives such as antioxidants. The thermoplastic polymer has typically a molecular weight (Mw) of more than 10,000 and a glass transition temperature (Tg) usually below room temperature. A wide variety of thermoplastic polymers are suitable for use in the present invention. Such thermoplastic polymers are preferably water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins.

The additional resin has typically a Mw below 5,000 and a Tg usually above room temperature, typical concentrations of the resin in a hot melt are in the range of 30-60%. The plasticizer has a low Mw of typically less than 1,000 and a Tg below room temperature, a typical concentration is 0-15%.

Preferably the adhesive is present in the forms of fibres throughout the absorbent structure, i.e. the adhesive is fiberized. Preferably, the fibres will preferably have an average thickness of 1-50 micrometer and an average length of 5 mm to 50 cm.

Preferably, the absorbent structure may have a density greater than about $0.4$ g/cm$^3$. Preferably, the density is greater than about $0.5$ g/cm$^3$, more preferably greater than about $0.6$ g/cm$^3$.

Preferred absorbent structures can for example be made as follows:

a) providing a substrate material, e.g. that can serve as a wrapping material;

b) depositing the water-absorbing material as described herein, comprising a coating of said polyurethane material herein, onto a first surface of the substrate material, c) depositing a absorbent fiber material and/or a thermoplastic and/or adhesive material onto the water-absorbing polymeric particulate material, d) and then typically closing the above structure by folding the substrate material over, or by placing another substrate material over the above, or by repeating step a) and b) and c) to form a second structure, that is placed onto the first structure, so that the coated particles and adhesive are sandwiched between the two substrate materials.

Preferred articles herein have a topsheet and a backsheet, which each have a front region, back region and crotch region, positioned therein between. The absorbent structure of the invention is typically positioned in between the topsheet and backsheet. Preferred backsheets are vapour pervious but liquid impervious. Preferred topsheet materials are liquid pervious, and/or for example at least partially hydrophilic; preferred are also so-called apertured topsheets. Preferred may be that the topsheet comprises a skin care composition, e.g. a lotion. Preferred are thin absorbent articles, such as adult and infant diapers, training pants, sanitary napkins comprising an absorbent structure of the invention, the articles having an average caliper (thickness) in the crotch region of less than 1.0 cm, preferably less than 0.7 cm, more preferably less than 0.5 cm, or even less than 0.3 cm (for this purpose alone, the crotch region being defined as the central zone of the product, when laid out flat and stretched, having a dimension of 20% of the length of the article and 50% of the width of the article).

A preferred diaper herein has a front waist band and a back waist band, whereby the front waist band and back waist band each have a first end portion and a second end portion and a middle portion located between the end portions, and whereby preferably the end portions comprise each a fastening system, to fasten the front waist band to the rear waist band or whereby preferably the end portions are connected to one another, and whereby the middle portion of the back waist band and/or the back region of the backsheet and/or the crotch region of the backsheet comprises a landing member, preferably the landing member comprising second engaging elements selected from loops, hooks, slots, slits, buttons, magnets. Most preferred are hooks, adhesive or cohesive second engaging elements. Preferred may be that the engaging elements on the article, or preferably diaper are provided with a means to ensure they are only engage able at certain moments, for example, they may be covered by a removable tab, which is removed when the engaging elements are to be engaged and may be re-closed when engagement is no longer needed, as described above. Preferred diapers, including training pants, herein have one or more sets of leg elastics and/or barrier leg cuffs, as known in the art.

The water-absorbing material herein, hereinafter also referred to as hydrogel-forming polymer, was tested by the test methods described herein below.

Methods:

The measurements should be carried out, unless otherwise stated, at an ambient temperature of 23±2° C. and a relative humidity of 50±10%. The water-absorbing polymeric particles are thoroughly mixed through before measurement. For the purpose of the following methods AGM means "Absorbent Gelling Material" and can relate to the water absorbing polymer particles as well as to the water-absorbing material. The respective meaning is clearly defined by the data given in the examples below. The test methods, for example for determining CRC, CS-CRC, AUL, CS-AUL, SFC, and CCRC are disclosed in WO 2006/082239 and are incorporated by reference. Measurement of FSR, FHA and CS-FSC is carried out as described below.

Saline Flow Conductivity (SFC)

The method to determine the permeability of a swollen gel layer is the "Saline Flow Conductivity" also known as "Gel Layer Permeability" and is described in EP A 640 330. The equipment used for this method has been modified as described below.

Figure 1:
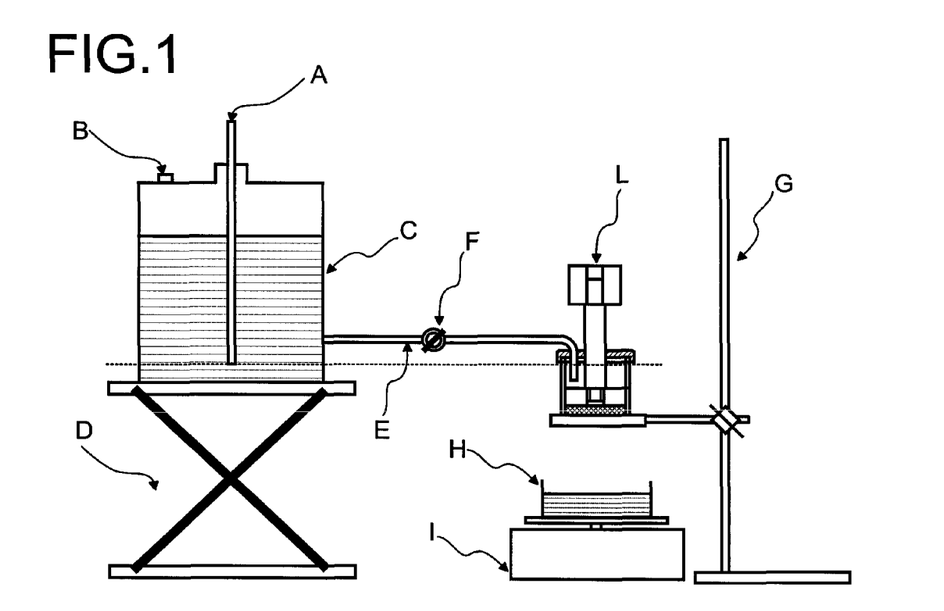
FIG. 1, FIG. 2, and FIG. 3 show equipment and equipment elements used herein to measure the SFC and CS-SFC of the water-absorbing herein.

FIG. 1 shows the permeability measurement equipment set-up with the open-ended tube for air admittance A, stoppered vent for refilling B, constant hydrostatic head reservoir C, Lab Jack D, delivery tube E, stopcock F, ring stand support G, receiving vessel H, balance I and the SFC apparatus L.

Figure 2:
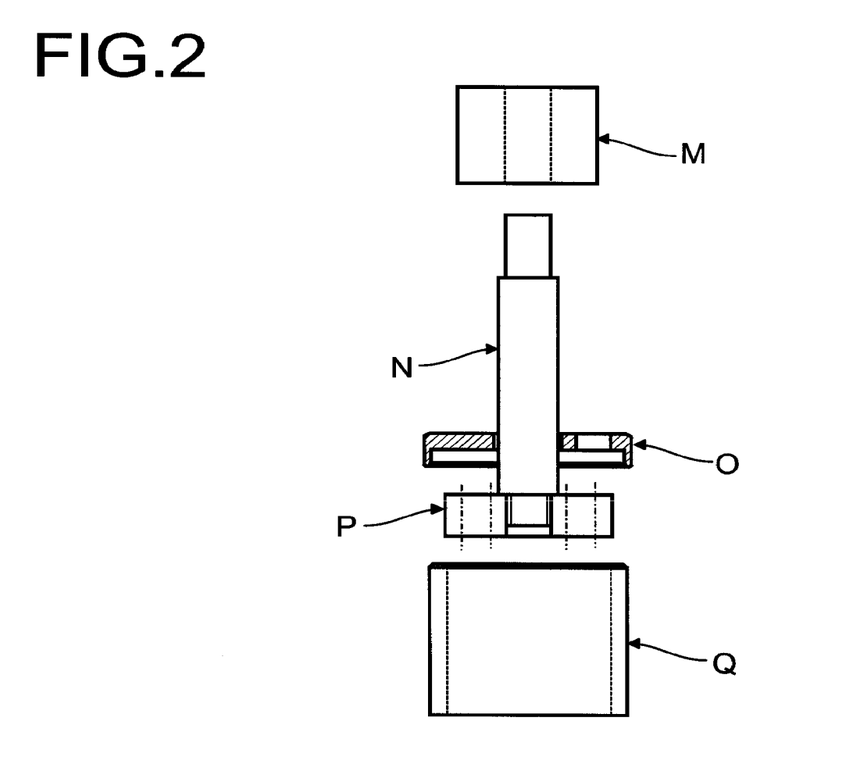

FIG. 2 shows the SFC apparatus L consisting of the metal weight M, the plunger shaft N, the lid O, the center plunger P and the cylinder Q.

The cylinder Q has an inner diameter of 6.00 cm (area=28.27 cm$^2$). The bottom of the cylinder Q is faced with a stainless-steel screen cloth (mesh width: 0.036 mm; wire diameter: 0.028 mm) that is bi-axially stretched to tautness prior to attachment. The plunger consists of a plunger shaft N of 21.15 mm diameter. The upper 26.0 mm having a diameter of 15.8 mm, forming a collar, a perforated center plunger P which is also screened with a stretched stainless-steel screen (mesh width: 0.036 mm; wire diameter: 0.028 mm), and annular stainless steel weights M. The annular stainless steel weights M have a center bore so they can slip on to plunger shaft and rest on the collar. The combined weight of the center plunger P, shaft and stainless-steel weights M must be 596 g (±6 g), which corresponds to 0.30 PSI over the area of the cylinder. The cylinder lid O has an opening in the center for vertically aligning the plunger shaft N and a second opening near the edge for introducing fluid from the reservoir into the cylinder Q.

Figure 3:
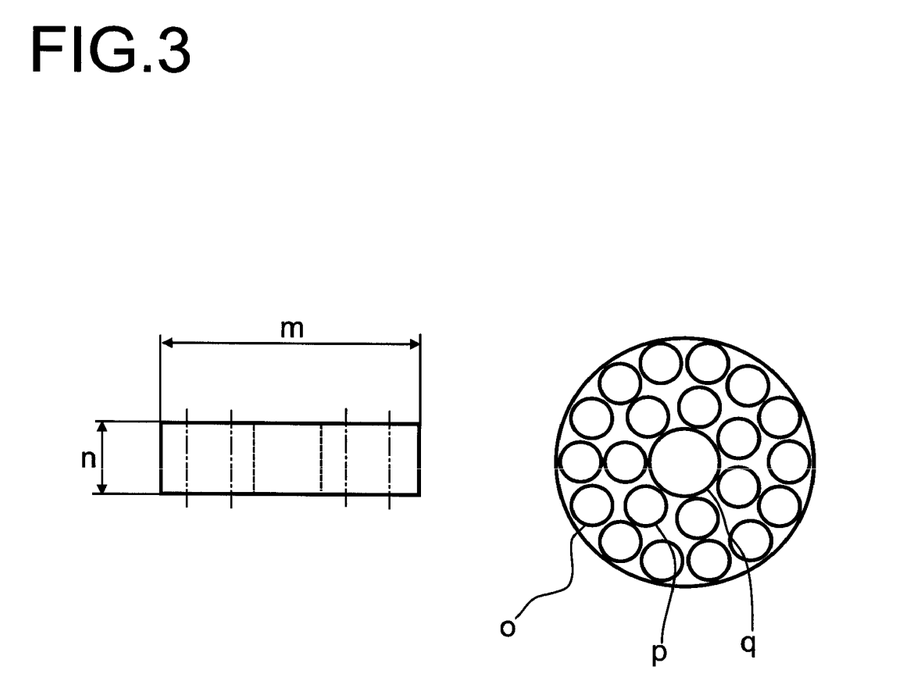

The cylinder Q specification details are:
Outer diameter of the Cylinder: 70.35 mm
Inner diameter of the Cylinder: 60.0 mm
Height of the Cylinder: 60.5 mm
The cylinder lid O specification details are:
Outer diameter of SFC Lid: 76.05 mm
Inner diameter of SFC Lid: 70.5 mm
Total outer height of SFC Lid: 12.7 mm
Height of SFC Lid without collar: 6.35 mm
Diameter of hole for Plunger shaft positioned in the center: 22.25 mm
Diameter of hole in SFC lid: 12.7 mm
Distance centers of above mentioned two holes: 23.5 mm
The metal weight M specification details are:
Diameter of Plunger shaft for metal weight: 16.0 mm
Diameter of metal weight: 50.0 mm
Height of metal weight: 39.0 mm
FIG. 3 shows the plunger center P specification details
Diameter m of SFC Plunger center: 59.7 mm
Height n of SFC Plunger center: 16.5 mm
14 holes o with 9.65 mm diameter equally spaced on a 47.8 mm bolt circle and 7 holes p with a diameter of 9.65 mm equally spaced on a 26.7 mm bolt circle ⅝ inches thread q.

Prior to use, the stainless steel screens of SFC apparatus, should be accurately inspected for clogging, holes or over stretching and replaced when necessary. An SFC apparatus with damaged screen can deliver erroneous SFC results, and must not be used until the screen has been fully replaced.

Measure and clearly mark, with a permanent fine marker, the cylinder at a height of 5.00 cm (±0.05 cm) above the screen attached to the bottom of the cylinder. This marks the fluid level to be maintained during the analysis. Maintenance of correct and constant fluid level (hydrostatic pressure) is critical for measurement accuracy.

A constant hydrostatic head reservoir C is used to deliver NaCl solution to the cylinder and maintain the level of solution at a height of 5.0 cm above the screen attached to the bottom of the cylinder. The bottom end of the reservoir air-intake tube A is positioned so as to maintain the fluid level in the cylinder at the required 5.0 cm height during the measurement, i.e., the height of the bottom of the air tube A from the bench top is the same as the height from the bench top of the 5.0 cm mark on the cylinder as it sits on the support screen above the receiving vessel. Proper height alignment of the air intake tube A and the 5.0 cm fluid height mark on the cylinder is critical to the analysis. A suitable reservoir consists of a jar containing: a horizontally oriented L-shaped delivery tube E for fluid delivering, an open-ended vertical tube A for admitting air at a fixed height within the reservoir, and a stoppered vent B for re-filling the reservoir. The delivery tube E, positioned near the bottom of the reservoir C, contains a stopcock F for starting/stopping the delivery of fluid. The outlet of the tube is dimensioned to be inserted through the opening in the cylinder lid O, with its end positioned below the surface of the fluid in the cylinder (after the 5 cm height is attained). The air-intake tube is held in place with an o-ring collar. The reservoir can be positioned on a laboratory jack D in order to adjust its height relative to that of the cylinder. The components of the reservoir are sized so as to rapidly fill the cylinder to the required height (i.e., hydrostatic head) and maintain this height for the duration of the measurement. The reservoir must be capable to deliver liquid at a flow rate of minimum 3 g/sec for at least 10 minutes.

Position the plunger/cylinder apparatus on a ring stand with a 16 mesh rigid stainless steel support screen (or equivalent). This support screen is sufficiently permeable so as to not impede fluid flow and rigid enough to support the stainless steel mesh cloth preventing stretching. The support screen should be flat and level to avoid tilting the cylinder apparatus during the test. Collect the fluid passing through the screen in a collection reservoir, positioned below (but not supporting) the support screen. The collection reservoir is positioned on a balance accurate to at least 0.01 g. The digital output of the balance is connected to a computerized data acquisition system.

Preparation of Reagents

Following preparations are referred to a standard 1 liter volume. For preparation multiple than 1 liter, all the ingredients must be calculated as appropriate.

Jayco Synthetic Urine

Fill a 1 L volumetric flask with de-ionized water to 80% of its volume, add a stir bar and put it on a stirring plate. Separately, using a weighing paper or beaker weigh (accurate to ±0.01 g) the amounts of the following dry ingredients using the analytical balance and add them into the volumetric flask in the same order as listed below. Mix until all the solids are dissolved then remove the stir bar and dilute to 1 L volume with distilled water. Add a stir bar again and mix on a stirring plate for a few minutes more. The conductivity of the prepared solution must be 7.6±0.23 mS/cm.

Chemical Formula Anhydrous Hydrated
Potassium Chloride (KCl) 2.00 g
Sodium Sulfate (Na2SO4) 2.00 g
Ammonium dihydrogen phosphate (NH4H2PO4) 0.85 g
Ammonium phosphate, dibasic ((NH4)2HPO4) 0.15 g
Calcium Chloride (CaCl2) 0.19 g (2H2O) 0.25 g
Magnesium chloride (MgCl2) 0.23 g (6H2O) 0.50 g To make the preparation faster, wait until total dissolution of each salt before adding the next one. Jayco may be stored in a clean glass container for 2 weeks. Do not use if solution becomes cloudy. Shelf life in a clean plastic container is 10 days.

0.118 M Sodium Chloride (NaCl) Solution

Using a weighing paper or beaker weigh (accurate to ±0.01 g) 6.90 g of sodium chloride into a 1 L volumetric flask and fill to volume with de-ionized water. Add a stir bar and mix on a stirring plate until all the solids are dissolved. The conductivity of the prepared solution must be 12.50±0.38 mS/cm.

Test Preparation

Using a reference metal cylinder (40 mm diameter; 140 mm height) set the caliper gauge (e.g. Mitotoyo Digimatic Height Gage) to read zero. This operation is conveniently performed on a smooth and level bench top. Position the SFC apparatus without AGM under the caliper gauge and record the caliper as L1 to the nearest of 0.01 mm.

Fill the constant hydrostatic head reservoir with the 0.118 M NaCl solution. Position the bottom of the reservoir air-intake tube A so as to maintain the top part of the liquid meniscus in the SFC cylinder at the required 5.0 cm height during the measurement. Proper height alignment of the air-intake tube A at the 5 cm fluid height mark on the cylinder is critical to the analysis.

Saturate an 8 cm fritted disc (7 mm thick; e.g. Chemglass Inc. #CG 201-51, coarse porosity) by adding excess synthetic urine on the top of the disc. Repeating until the disc is saturated. Place the saturated fritted disc in the hydrating dish and add the synthetic urine until it reaches the level of the disc. The fluid height must not exceed the height of the disc.

Place the collection reservoir on the balance and connect the digital output of the balance to a computerized data acquisition system. Position the ring stand with a 16 mesh rigid stainless steel support screen above the collection dish. This 16 mesh screen should be sufficiently rigid to support the SFC apparatus during the measurement. The support screen must be flat and level.

AGM Sampling

AGM samples should be stored in a closed bottle and kept in a constant, low humidity environment. Mix the sample to evenly distribute particle sizes. Remove a representative sample of material to be tested from the center of the container using the spatula. The use of a sample divider is recommended to increase the homogeneity of the sample particle size distribution.

SFC Procedure

Position the weighing funnel on the analytical balance plate and zero the balance. Using a spatula weigh 0.9 g (±0.05 g) of AGM into the weighing funnel. Position the SFC cylinder on the bench, take the weighing funnel and gently, tapping with finger, transfer the AGM into the cylinder being sure to have an evenly dispersion of it on the screen. During the AGM transfer, gradually rotate the cylinder to facilitate the dispersion and get homogeneous distribution. It is important to have an even distribution of particles on the screen to obtain the highest precision result. At the end of the distribution the AGM material must not adhere to the cylinder walls. Insert the plunger shaft into the lid central hole then insert the plunger center into the cylinder for few centimeters. Keeping the plunger center away from AGM insert the lid in the cylinder and carefully rotate it until the alignment between the two is reached. Carefully rotate the plunger to reach the alignment with lid then move it down allowing it to rest on top of the dry AGM. Insert the stainless steel weight to the plunger rod and check if the lid moves freely. Proper seating of the lid prevents binding and assures an even distribution of the weight on the gel bed.

The thin screen on the cylinder bottom is easily stretched. To prevent stretching, apply a sideways pressure on the plunger rod, just above the lid, with the index finger while grasping the cylinder portion of the apparatus. This "locks" the plunger in place against the inside of the cylinder so that the apparatus can be lifted. Place the entire apparatus on the fitted disc in the hydrating dish. The fluid level in the dish should not exceed the height of the fitted disc. Care should be taken so that the layer does not loose fluid or take in air during this procedure. The fluid available in the dish should be enough for all the swelling phase. If needed, add more fluid to the dish during the hydration period to ensure there is sufficient synthetic urine available. After a period of 60 minutes, place the SFC apparatus under the caliper gauge and record the caliper as L2 to the nearest of 0.01 mm. Calculate, by difference L2−L1, the thickness of the gel layer as L0 to the nearest ±0.1 mm. If the reading changes with time, record only the initial value.

Transfer the SFC apparatus to the support screen above the collection dish. Be sure, when lifting the apparatus, to lock the plunger in place against the inside of the cylinder. Position the constant hydrostatic head reservoir such that the delivery tube is placed through the hole in the cylinder lid. Initiate the measurement in the following sequence:

a) Open the stopcock of the constant hydrostatic head reservoir and permit the fluid to reach the 5 cm mark. This fluid level should be obtained within 10 seconds of opening the stopcock.

b) Once 5 cm of fluid is attained, immediately initiate the data collection program.

With the aid of a computer attached to the balance, record the quantity of fluid passing through the gel layer versus time at intervals of 20 seconds for a time period of 10 minutes. At the end of 10 minutes, close the stopcock on the reservoir. The data from 60 seconds to the end of the experiment are used in the calculation. The data collected prior to 60 seconds are not included in the calculation. Perform the test in triplicate for each AGM sample.

Evaluation of the measurement remains unchanged from EP-A 640 330. Through-flux is captured automatically.

Saline flow conductivity (SFC) is calculated as follows:

SFC[cm$^3$s/g]=($Fg(t=0) \times L_0$)/($d \times A \times WP$), where Fg(t=0) is the through-flux of NaCl solution in g/s, which is obtained from a linear regression analysis of the Fg(t) data of the through-flux determinations by extrapolation to t=0, $L_0$ is the thickness of the gel layer in cm, d is the density of the NaCl solution in g/cm$^3$, A is the area of the gel layer in cm$^2$ and WP is the hydrostatic pressure above the gel layer in dyn/cm$^2$.

CS-SFC (Core Shell Saline Flow Conductivity)

CS-SFC is determined completely analogously to SFC, with the following changes:

To modify the SFC the person skilled in the art will design the feed line including the stopcock in such a way that the hydrodynamic resistance of the feed line is so low that prior to the start of the measurement time actually used for the evaluation an identical hydrodynamic pressure as in the SFC (5 cm) is attained and is also kept constant over the duration of the measurement time used for the evaluation.

the weight of AGM used is 1.50+/−0.05 g a 0.9% by weight sodium chloride solution is used as solution to preswell the AGM sample and for through-flux measurement the preswell time of the sample for measurement is 240 minutes for preswelling, a filter paper 90 mm in diameter (Schleicher & Schüll, No 597) is placed in a 500 ml crystallizing dish (Schott, diameter=115 mm, height=65 mm) and 250 ml of 0.9% by weight sodium chloride solution are added, then the SFC measuring cell with the sample is placed on the filter paper and swelling is allowed for 240 minutes the through-flux data are recorded every 5 seconds, for a total of 3 minutes the points measured between 10 seconds and 180 seconds are used for evaluation and Fg(t=0) is the through-flux of NaCl solution in g/s which is obtained from a linear regression analysis of the Fg(t) data of the through-flux determinations by extrapolation to t=0 the stock reservoir bottle in the SFC-measuring apparatus for through-flux solution contains about 5 kg of sodium chloride solution.

Data obtained is herein referred to as CS-SFC.

Free Swell Rate (FSR)

1.00 g (=W1) of the dry water-absorbing polymeric particles is weighed into a 25 ml glass beaker and is uniformly distributed on the base of the glass beaker. 20 ml of a 0.9% by weight sodium chloride solution are then dispensed into a second glass beaker, the contents of this beaker are rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

FSR[g/gs]=$W2/(W1 \times t)$

When the moisture content of the base polymer is more than 3% by weight, however, the weight W1 must be corrected for this moisture content.

Fixed Height Absorption (FHA)

The FHA is a method to determine the ability of a swollen gel layer to transport fluid by wicking. It is executed and evaluated as described on page 9 and 10 in EP 01 493 453 A1.

The following adjustments need to be made versus this description:

Laboratory conditions are 23±2° C. and relative humidity is no more than 50%.

Glass frit: 500 ml glass frit P40, as defined by ISO 4793, nominal pore size 16-40 µm, thickness 7 mm, e.g. Duran Schott pore size class 3. At 20° C.: a 30 cm diameter disk must be capable of a water flow of 50 ml/min for a pressure drop of 50 mbar.

Flexible plastic Tygon tube, for connecting the reparatory funnel with the funnel with frit. Length must be sufficient to allow for 20 cm vertical movement of the funnel.

Use of high wet strength cellulose tissue, maximum basis weight 24.6 g/cm$^2$, size 80×80 mm, minimum wet tensile strength 0.32 N/cm (CD direction), and 0.8 N/cm (MD direction), e.g. supplied by Fripa Papierfabrik Albert Friedrich KG, D-63883 Miltenberg.

The tissue is clamped with a metal ring on the bottom side of the sample holder.

Calculation:

FHA=($m3-m2$)÷($m2-m1$)

weight of absorbed saline solution per 1 g of AGM, with m1=weight of empty sample holder in g,
m2=weight of sample holder with dry AGM in g,
m3=weight of sample holder with wet AGM in g.

FHA is only determined in the context of the present invention with a hydrostatic column pressure corresponding to FHA at 20 cm.

The following examples illustrate the invention without limiting it.

Example 1

Synthesis of the Base Polymer

A Loedige VT 5R-MK plowshare kneader of 5l capacity was charged with 206.5 g of deionized water, 271.6 g of acrylic acid, 2115.6 g of 37.3 wt.-% sodium acrylate solution (100 mole % neutralized) and 3.5 g of a threefold ethoxylated glycerol triacrylate crosslinker and inertized by bubbling nitrogen through it for 20 minutes. This was followed by the addition of dilute aqueous solutions of 2.453 g of sodium persulfate (dissolved in 13.9 g of water), 0.053 g of ascorbic acid (dissolved in 10.46 g of water) and also 0.146 g of 30% by weight hydrogen peroxide (dissolved in 1.31 g of water) to initiate the polymerization at about 20° C. After initiation, the temperature of the heating jacket was controlled in order to monitor the temperature inside the reactor. The temperature was kept below 90° C. The obtained crumbly gel was dried in a circulating air drying cabinet at 160° C. for about 3 hours. The dried base polymer was subjected to milling and classified to 150 to 710 µm by sieving off over- and undersize particles.

Example 2

Post-Crosslinking

A post-crosslinking solution was used which contained in water/isopropanol (69.1/30.9):

0.14 wt.-% of a solution (50 wt.-%) of 2-hydroxyethyl oxazolidinone in 1,3-propanediol 0.7 wt.-% 1,2-propanediol 50 ppm (based on polymer) of sorbitan monooleate (2 wt.-% solution in water)

A Loedige VT 5R-MK plowshare kneader was charged with 1200 g of the base polymer and heated to a product temperature of 185° C. Subsequently, 4.55 wt.-% (based on polymer) of the post-crosslinking solution was sprayed on the polymer by means of nitrogen (0.5 bar) at 185° C. and a rotating speed of 200 rpm using a 2-fluid nozzle. After the spray-coating the mixing was continued for 40 minutes. The obtained product was classified to 710 μm and is designated as precursor.

Example 3

Reference Example

Coating of the Precursor:

In a cylindric fluidized bed (diameter of 150 mm having a sparger plate with 2 mm orifices) 2000 g of the precursor were coated with a mixture of 52.6 g of 37 wt.-% polyurethane dispersion (Astacin® Finish PUMN TF) and 47.4 g of water at 35° C. Subsequently, the coated precursor was coated in the same fluidized bed under the same conditions with a mixture of 20 g Levasil, 50/50 (15 wt.-% of a silica dispersion) and 30 g of water. A Loedige M5 plowshare mixer M5 was then charged with 1200 g of the obtained coated precursor and then heated to 180° C. product temperature and kept for 20 minutes. The obtained product is the reference sample.

After cooling the following parameters were determined:
FHA: 3.8 g/g
FSR: 0.14 g/g·s
CS-FSC: $410 \cdot 10^{-7}$ cm$^3$s/g.

Example 4

Coating of the Precursor According to the Invention

The same fluidized bed as used in example 3 was charged with 2000 g precursor and coated with a mixture of 52.6 g of a 37 wt.-% polyurethane dispersion (Astacin® Finish PUMN TF), 30 g Acematt TS 100 (pyrogenic silica powder) and 570 g of water at 35° C. Subsequently, a Loedige M5 plowshare mixer M5 was charged with 1200 g of the obtained coated precursor and heated to a product temperature of 180° C. and kept for 20 minutes. After cooling FHA and FSR were determined:
FHA: 9.1 g/g
FSR: 0.20 g/g·s
CS-FSC: $265 \cdot 10^{-7}$ cm$^3$s/g.

Example 5

Coating of the Precursor According to the Invention

The same fluidized bed as used in example 3 was charged with 2000 g precursor and coated with a mixture of 52.6 g of a 37 wt.-% polyurethane dispersion (Astacin® Finish PUMN TF), 40 g Acematt TS 100 (pyrogenic silica powder) and 760 g of water at 35° C. Subsequently, a Loedige M5 plowshare mixer M5 was charged with 1200 g of the obtained coated precursor and heated to a product temperature of 180° C. and kept for 20 minutes. After cooling FHA and FSR were determined:

FHA: 13.8 g/g
FSR: 0.21 g/g·s
CS-FSC: $270 \cdot 10^{-7}$ cm$^3$s/g.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent structure comprising a water-absorbing material containing coated water-absorbing polymer particles, the absorbent structure being suitable for absorption and retention of bodily fluids, and being produced by a process comprising the steps of:
   a) coating water-absorbing polymer particles with an aqueous composition comprising a film-forming polyurethane and pyrogenic silica in a weight ratio from about 1:1 to about 1:4; and
   b) heat-treating the coated particles at above 50° C.

2. An absorbent structure as in claim 1, wherein the film-forming polyurethane and the pyrogenic silica are used in a weight ratio from about 1:1.3 to about 1:3.

3. An absorbent structure as in claim 1, wherein the film-forming polyurethane and the pyrogenic silica are used in a weight ratio from about 1:1.2 to about 1:3.

4. An absorbent structure as in claim 1, wherein the polyurethane is a polyester polyol polyurethane.

5. An absorbent article as in claim 1, wherein step a) is a spray-coating step and the resulting coating is a spray coating.

6. An absorbent structure as in claim 1, wherein the heat-treating is carried out at a temperature from about 100° C. to about 200° C.

7. An absorbent structure as in claim 1, whereby the water-absorbing polymers comprise cross-linked polyacrylic acid/polyacrylate polymers.

8. An absorbent structure as in claim 7, wherein the crosslinking is done with an acrylate ester of a polyalcohol crosslinker.

9. An absorbent structure of claim 8, wherein said crosslinker is the triacrylate of ethoxylated glycerine.

10. An absorbent structure as in claim 1, wherein the water-absorbing polymer particles are surface crosslinked with a post-crosslinker.

11. An absorbent structure as in claim 10, wherein the post-crosslinker comprises 2-oxazolidinone or N-(2-hydroxyethyl)oxazolidin-2-one.

12. An absorbent article comprising the absorbent structure of claim 1.

13. An absorbent article as in claim 12, selected from the group consisting of an infant diaper, an adult diaper, and a sanitary napkin.

14. An absorbent structure comprising a water-absorbing material containing water-absorbing polymer particles, coated with a film-coating of a film-forming polyurethane and pyrogenic silica, incorporated in said polyurethane film coating, in a weight ratio from about 1:1 to about 1:4, the absorbent structure being suitable for absorption and retention of bodily fluids.

15. An absorbent structure as in claim 14, wherein the film-forming polyurethane and the pyrogenic silica are used in a weight ratio from about 1:1.3 to about 1:3.

16. An absorbent structure as in claim 14, wherein the polyurethane is a polyester polyol polyurethane.

17. An absorbent structure as in claim 14, whereby the water-absorbing polymers comprise cross-linked polyacrylic acid/polyacrylate polymers.

18. An absorbent structure as in claim 17, wherein the crosslinking is done with an acrylate ester of a polyalcohol crosslinker.

19. An absorbent structure as in claim 18, wherein said crosslinker is the triacrylate of ethoxylated glycerine.

20. An absorbent structure as in claim 14, wherein the water-absorbing polymer particles are surface crosslinked with a post-crosslinker.

21. An absorbent structure as in claim 20, wherein the post-crosslinker comprises 2-oxazolidinone or N-(2-hydroxyethyl)oxazolidin-2-one.

22. An absorbent article comprising the absorbent structure of claim 14.

23. An absorbent article as in claim 22, selected from the group consisting of an infant diaper, an adult diaper, and a sanitary napkin.

24. An absorbent structure as in claim 14, wherein the film-forming polyurethane and the pyrogenic silica are used in a weight ratio from about 1:1.2 to about 1:3.

25. An absorbent structure as in claim 1, wherein the water-absorbing polymer material exhibits a Fixed Height Absorption (FHA) of at least 5 g/g and a Free Swell Rate (FSR) of at least 0.17 g/g·s.

26. An absorbent structure as in claim 25, wherein the water-absorbing polymer material exhibits an FHA of at least 10 g/g and an FSR of at least 0.20 g/g·s.

27. An absorbent structure as in claim 1, wherein the water-absorbing polymer material exhibits a core shell saline flow conductivity (CS-SFC) of at least $100 \cdot 10^{-7}$ cm$^3$s/g.

28. An absorbent structure as in claim 27, wherein the water-absorbing polymer material exhibits a CS-SFC of at least $200 \cdot 10^{-7}$ cm$^3$s/g.

29. An absorbent structure as in claim 14, wherein the water-absorbing polymer material exhibits an FHA of at least 5 g/g and an FSR of at least 0.17 g/g·s.

30. An absorbent structure as in claim 29, wherein the water-absorbing polymer material exhibits an FHA of at least 10 g/g and an FSR of at least 0.20 g/g·s.

31. An absorbent structure as in claim 14, wherein the water-absorbing polymer material exhibits a CS-SFC of at least $100 \cdot 10^{-7}$ cm$^3$s/g.

32. An absorbent structure as in claim 31, wherein the water-absorbing polymer material exhibits a CS-SFC of at least $200 \cdot 10^{-7}$ cm$^3$s/g.

* * * * *